(12) United States Patent
Codner et al.

(10) Patent No.: US 10,028,897 B2
(45) Date of Patent: Jul. 24, 2018

(54) REMOVABLE TATTOO INK AND THE USE THEREOF

(71) Applicant: ULTRA INK, INC., Atlanta, GA (US)

(72) Inventors: Blake Codner, Atlanta, GA (US); Mark Codner, Atlanta, GA (US); Tianhe Zhang, Norcross, GA (US); Cong Guo, Collegeville, PA (US); Anthony Guebert, Atlanta, GA (US); Xujing Sun, Alpharetta, GA (US)

(73) Assignee: ULTRA INK, INC., Atlanta, GA (US)

( * ) Notice: Subject to any disclaimer, the term of this patent is extended or adjusted under 35 U.S.C. 154(b) by 198 days.

(21) Appl. No.: 14/435,659

(22) PCT Filed: Oct. 15, 2013

(86) PCT No.: PCT/US2013/065071
§ 371 (c)(1),
(2) Date: Apr. 14, 2015

(87) PCT Pub. No.: WO2014/062689
PCT Pub. Date: Apr. 24, 2014

(65) Prior Publication Data
US 2015/0265508 A1    Sep. 24, 2015

Related U.S. Application Data

(60) Provisional application No. 61/714,097, filed on Oct. 15, 2012.

(51) Int. Cl.
*C09D 11/00*    (2014.01)
*C09D 139/02*    (2006.01)
(Continued)

(52) U.S. Cl.
CPC .............. *A61K 8/11* (2013.01); *A61K 8/0241* (2013.01); *A61K 8/817* (2013.01); *A61K 8/8117* (2013.01);
(Continued)

(58) Field of Classification Search
CPC .... C09D 11/00; C09D 139/02; C09D 141/00; A61Q 1/025; A61N 5/062; A61K 8/11;
(Continued)

(56) References Cited

U.S. PATENT DOCUMENTS 4,159,659 A    7/1979    Nightingale et al.
5,445,611 A    8/1995    Eppstein et al.
(Continued)

FOREIGN PATENT DOCUMENTS

EP    1593374 A1    11/2005
EP    1107724 B1    12/2006
(Continued)

OTHER PUBLICATIONS

English translation of RU 2369386, Oct. 2009; 13 pages.*
(Continued)

*Primary Examiner* — Helene Klemanski
(74) *Attorney, Agent, or Firm* — Johnson, Marcou & Isaacs, LLC

(57) ABSTRACT

Provided is a removable tattoo ink that is composed of colored micro-particles that create permanent tissue markings, such as tattoos. The micro-particles include an inner core housing a bio-absorbable chromophore and an outer shell, which includes polystyrene sulfonate and polyallylamine hydrochloride and is designed for rupture with ultrasonic energy. The micro-particles can be implanted in the tissue of a subject, for example to create a tattoo and
(Continued)

ruptured in situ by the application of ultrasonic energy to remove the tattoo. Also provided are methods of making the colored micro-particles.

17 Claims, 7 Drawing Sheets

(51) Int. Cl.
| | |
|---|---|
| *C09D 141/00* | (2006.01) |
| *C09B 67/00* | (2006.01) |
| *A61K 8/11* | (2006.01) |
| *A61K 8/81* | (2006.01) |
| *A61N 5/06* | (2006.01) |
| *A61Q 1/02* | (2006.01) |
| *B01J 13/10* | (2006.01) |
| *B01J 13/22* | (2006.01) |
| *B01J 13/20* | (2006.01) |
| *C09B 67/02* | (2006.01) |
| *A61K 8/02* | (2006.01) |
| *C09B 67/22* | (2006.01) |
| *C08K 5/41* | (2006.01) |
| *C08K 9/10* | (2006.01) |
| *A61B 90/00* | (2016.01) |

(52) U.S. Cl.
CPC .............. *A61N 5/062* (2013.01); *A61Q 1/025* (2013.01); *B01J 13/10* (2013.01); *B01J 13/203* (2013.01); *B01J 13/22* (2013.01); *C08K 5/41* (2013.01); *C09B 67/0041* (2013.01); *C09B 67/0097* (2013.01); *C09D 11/00* (2013.01); *C09D 139/02* (2013.01); *C09D 141/00* (2013.01); *A61B 2090/3937* (2016.02); *A61K 2800/412* (2013.01); *A61K 2800/43* (2013.01); *A61K 2800/624* (2013.01); *A61K 2800/652* (2013.01); *A61K 2800/82* (2013.01); *C08K 9/10* (2013.01)

(58) Field of Classification Search
CPC .... A61K 8/0241; A61K 8/8117; A61K 8/817; A61K 2800/412; A61K 2800/43; B01J 13/10; B01J 13/22; C09B 67/0097
USPC ...................................... 106/31.03
See application file for complete search history.

(56) References Cited

U.S. PATENT DOCUMENTS

| | | | |
|---|---|---|---|
| 5,472,449 A | 12/1995 | Chou et al. | |
| 6,013,122 A | 1/2000 | Klitzman et al. | |
| 6,192,890 B1 | 2/2001 | Levy et al. | |
| 6,303,102 B1 | 10/2001 | Schlichte | |
| 6,458,192 B1 | 10/2002 | Tsujio et al. | |
| 6,800,122 B2 | 10/2004 | Anderson et al. | |
| 6,814,760 B2 | 11/2004 | Anderson et al. | |
| 6,881,249 B2 | 4/2005 | Anderson et al. | |
| 7,101,575 B2* | 9/2006 | Donath ............... | A61K 9/5026 424/489 |
| 7,175,950 B2 | 2/2007 | Anderson et al. | |
| 7,285,364 B2 | 10/2007 | Anderson et al. | |
| 7,435,524 B2 | 10/2008 | Anderson et al. | |
| 2002/0187197 A1 | 12/2002 | Caruso | |
| 2007/0107625 A1 | 5/2007 | Anderson et al. | |
| 2007/0224264 A1* | 9/2007 | Antipov ............... | A61K 9/0009 424/463 |
| 2009/0304756 A1 | 12/2009 | Dähne | |
| 2009/0325221 A1 | 12/2009 | Long et al. | |

FOREIGN PATENT DOCUMENTS

| | | |
|---|---|---|
| JP | 2003511281 A | 3/2003 |
| JP | 2007516238 A | 6/2007 |
| RU | 2369386 C2 | 10/2009 |
| WO | 9947252 A2 | 9/1999 |
| WO | 2007146988 A1 | 12/2007 |

OTHER PUBLICATIONS

Extended European Search Report for European Patent Application No. 13847287.3, dated Mar. 21, 2016, 8.
Australian Examination Report for Australian Patent Application No. 2013331432, dated May 18, 2016, 4.
2nd Examination Report for Australian Patent Application No. 2013331432, dated Dec. 13, 2016, 3.
De Geest, "Ultrasound-Triggered Release from Multilayered Capsules", Wiley InterScience, vol. 3, No. 5, 2007, 804-808.
Kalinina, International Search Report and Written Opinion for counterpart PCT Application No. PCT/US2013/065071, dated Feb. 20, 2014, 1-7.
European Office Action for European Patent Application No. 13847287.3, dated Apr. 20, 2017, 5 pages.
Japanese Office Action for Japanese Patent Application No. 2015-537008, dated Jul. 11, 2017, 2 pages.
Chaudhary, et al., "Evaluation of Glucose Sensitive Affinity Binding Assay Entrapped in Fluorescent Dissolved-Core Alginate Microspheres", Biotechnoloy and Bioengineering, vol. 104, No. 6, Dec. 15, 2009, 1075-1085.
Corso, "Three in Ten Americans with a Tattoo Say Having One Makes Them Feel Sexier,", Harris Poll, Feb. 2008, 7 pages.
Pew Research Center Survey, "Millennials' Judgements About Recent Trends Not So Different", The Pew Research Center for the People & The Press, Jan. 7, 2010, 3 pages.

* cited by examiner

Week1　　　　　　　　　Week8

Week1　　　　　　　　　Week2

Week 2　　　　　　　　　Week 7

REMOVABLE TATTOO INK AND THE USE THEREOF

CROSS-REFERENCE TO RELATED APPLICATION

This application is the U.S. National Stage of International Application No. PCT/US2013/065071, filed Oct. 15, 2013, published in English under PCT Article 21(2), which claims the priority benefit of the earlier filing date of U.S. Provisional Application No. 61/714,097, filed on Oct. 15, 2012, which is incorporated by reference herein in its entirety.

FIELD OF THE DISCLOSURE

This disclosure relates generally to tattoo ink and more specifically to tattoo ink that can be removed with the application of ultrasonic energy and the use thereof.

BACKGROUND

Tattooing involves the placement of pigment into the skin's dermis, the layer of dermal tissue underlying the epidermis. After initial injection, pigment is dispersed throughout a homogenized damaged layer down through the epidermis and upper dermis. As healing proceeds, the damaged epidermis flakes away (eliminating surface pigment) while deeper in the skin granulation tissue forms, which is later converted to connective tissue by collagen growth. This mends the upper dermis, where pigment remains trapped within fibroblasts, ultimately concentrating in a layer just below the dermis/epidermis boundary.

The most common method of tattooing in modern times is the electric tattoo machine, which inserts ink into the skin via a single needle or a group of needles that are soldered onto a bar, which is attached to an oscillating unit. The unit rapidly and repeatedly drives the needles in and out of the skin, usually 80 to 150 times a second. A significant number of individuals have tattoos making up approximately 15% of the world population.

The demand for tattoos continues to increase primarily for body art adornment, however tattoos are also used for religious, cultural, and medical indications. Sixteen percent of the tattoo consumers have been shown to eventually regret their tattoos, which is approximately 6.5 million people in the U.S. (Corso RA. Three in Ten Americans with Tattoo Say Having One Makes Them Feel Sexier. The Harris Poll. 2008). More than half of tattoo users are in the age group of 25-40 years of age with no significant difference between the number of male and female tattoo consumers (Corso RA. Three in Ten Americans with Tattoo Say Having One Makes Them Feel Sexier. The Harris Poll. 2008).

Currently, the most common and most effective technique for tattoo removal is high energy lasers. However, laser treatments require a long period of time and multiple sessions for substantial removal and a cost up to $10,000 (Millennials' Judgments about Recent Trends Not So Different. Pew Research Center for the People and the Press. 2010). Laser treatments are also painful and have poor results often resulting in burn scars and smudged tattoos that are incompletely removed. According to the 2010 statistics of the U.S. Census Bureau, there were 1,430 establishments in the U.S. in the category of "tattoo services" with total revenue of about $200 million. (2007 Economic Census. U.S. Census Bureau. Updated 2010. Accessed Jun. 27, 2011). However, there are only 88 establishments in the category of "tattoo removal services" with revenue of $6 million (2007 Economic Census. U.S. Census Bureau. Updated 2010. Accessed Jun. 27, 2011).

Since current tattoo removal methods have not been overly successful, developing a non-permanent tattoo ink that is easily removable by a less expensive and painless removal method may be an optimal solution. Consumers should have the option of leaving no reminiscence of their tattoos while the manufacturers, tattoo artists, and doctors can profit financially from the popularity of this new ink. Therefore, there exists a need for tattoo inks that are amenable to removal. This disclosure meets this need.

SUMMARY OF THE DISCLOSURE

There exists a large demand for a new tattoo ink which can be easily removed, which is inexpensive, and is a painless alternative to current laser removal. The present disclosure meets that need by providing UltraInk™ a new tattoo ink formed by encapsulation of non-toxic, bio-absorbable chromophores, such as food coloring, within a translucent outer shell that can be broken by the application of ultrasonic energy. The resultant micro-particles have the appearance, consistency, color and microscopic size similar to conventional tattoo ink. Thus, disclosed herein is a removable tattoo ink, that comprises colored micro-particles. In some embodiments, the micro-particles comprise an internal core, comprising one or more bio-absorbable chromophores and an outer shell, comprising at least one layer of polystyrene sulfonate (PSS) and at least one layer of polyallylamine hydrochloride (PAH). This outer shell is configured to be rupturable by the application of electromagnetic radiation in the ultrasonic range. In some embodiments, the outer shell is further coated with polystyrene. The outer shell and the optional coating were developed to be substantially visibly transparent such that the chromophore is detectable through the outer shell and/or coating.

Also disclosed is a method of applying a removable tissue marking, such as a tattoo. In certain embodiments, the method comprises providing a disclosed removable tattoo ink and implanting the ink into a tissue of a subject, for example using a conventional tattoo machine, thereby forming a tissue marking. Also disclosed is a method for rendering undetectable a tissue marking implanted in tissue. The method comprising subjecting a tissue marking formed from a disclosed removable tattoo ink with ultrasonic radiation for an intensity and duration sufficient to disrupt the micro-particles of the removable tattoo ink, thereby rendering undetectable the tissue marking implanted in tissue.

Further disclosed is a method of making a removable tattoo ink. The method comprising forming an internal core, comprising one or more bio-absorbable chromophores and one or more salts with low water solubility and coating the internal core with at least one layer of polystyrene sulfonate (PSS) and at least one layer of polyallylamine hydrochloride (PAH). In some embodiments, the method further includes removing the one or more salts with low water solubility, such that the inner core is substantially the one or more bio-absorbable chromophores.

The foregoing and other features and advantages of the disclosure will become more apparent from the following detailed description, which proceeds with reference to the accompanying figures.

DETAILED DESCRIPTION

I. Summary of Terms

Figure 1:
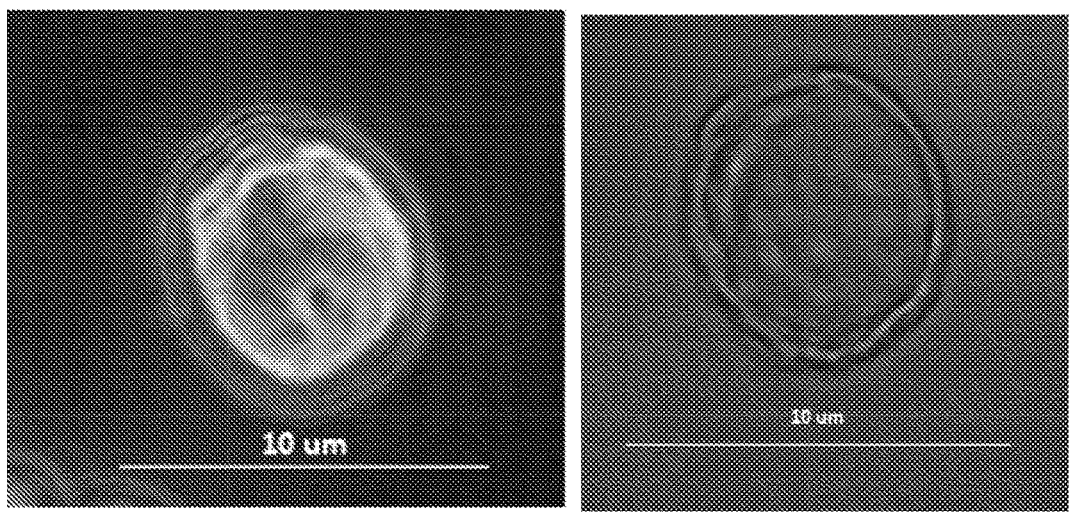
FIG. 1 is a pair of digital images showing a comparison of a micro-particle with no dye loaded into it with the $Ca_2CO_3$ core (left) and without the $Ca_2CO_3$ core (right).

Unless otherwise noted, technical terms are used according to conventional usage. As used herein, the singular forms "a," "an," and "the," refer to both the singular as well as plural, unless the context clearly indicates otherwise. As used herein, the term "comprises" means "includes." Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Chromophore: is a substance that has color or imparts a color to micro-particles, for example by virtue of being inside a hollow micro-particle.

Color: is broadly defined herein as a detectable (that is, visible or able to be made visible under certain lighting conditions, or able to be detected using a device, for example, an infrared camera) property determined by a substance's electromagnetic absorption and/or emission spectrum (that is, in the ultraviolet, near-ultraviolet, visible, near-infrared, infrared, and other ranges). Black and white are colors under this definition.

Micro-particle: A particle of a relatively small size, that can be implanted to form tissue markings and thus can be less than 50 nm to 100 microns or greater. Micro-particles are also large enough on average and have a configuration on average such that when a plurality is implanted into tissue a sufficient number is retained to form a detectable marking, even though some number of the individual micro-particles may be relocated from the tissue marking site.

Subject: An animal, including both human and veterinary subjects

Tattoo: A type of tissue marking where the tissue is typically the skin.

Tissue marking: A mark created by the introduction of micro-particles disclosed herein into tissue, typically living tissue. Markings can be any color and must be detectable. The tissue markings, such as tattoos, of the present disclosure generally remain visible or otherwise detectable until it is exposed to ultrasonic energy.

Unless otherwise defined, all technical and scientific terms used herein have the same meaning as commonly understood by one of ordinary skill in the art to which this invention belongs.

II. Description of Several Embodiments

A. Introduction

The disclosed tattoo ink compositions, termed UltraInk™ because they are removable with ultrasonic energy, were synthesized after several prototype iterations, resulting in the current ink design which includes translucent micro-particles filled with a chromophore that are approximately equal in size and consistency to the current conventional permanent tattoo inks which are typically made of heavy metals. The relative size of the particle in the dermis makes the ink permanent (unless removed using ultrasonic energy) as macrophage cells are unable to remove the particle from the dermis because it is too large for the macrophage to remove to the lymphatic system.

The disclosed UltraInk™ compositions are made from an inner core synthesized with a combination of non-toxic bio-absorbable chromophores such as FD&C Blue No. 1 and FD&C Red No. 40, and a low solubility salt, such as $Ca_2CO_3$ followed by clear encapsulation with polyallylamine hydrochloride (PAH) and polystyrene sulfonate (PSS). Once the micro-particle encapsulation is complete, the solid salt is removed from the core, for example with water and/or EDTA, leaving the liquid core of color inside the clear micro-particle. The studies disclosed herein have described a detailed protocol to create and synthesize UltraInk™ using non-toxic coloring with a wide range of encapsulation layers. The synthesis of UltraInk™ was performed safely in a standard laboratory.

The animal studies disclosed herein demonstrate that UltraInk™ can be removed using ultrasonic energy with clearly defined advantages over laser removal. UltraInk™ thus provides an option to conventional permanent tattoo inks providing future consumers with an alternative that may be permanent or removable which has tremendous advantages to meet the continued demand for tattoos in the younger population and the documented significant rate of regret and demand for tattoo removal in the maturing population.

The compositions and methods disclosed herein provide several advantages over standard tattoos and their removal.

Standard tattoos are made using unregulated pigments of undisclosed nature which, once implanted, are in direct contact with living tissue for the recipient's life, even if no longer visible at the tissue marking site. The disclosed tattoo inks can reduce short- and long-term health risks associated with standard tattoo pigments. For example, in contrast to tattoo inks derived from heavy metals, the micro-particles are inert and non-toxic when implanted in tissue. A course of many treatments to remove a standard tattoo is not always successful, yet it is time-consuming and expensive, may expose the tissue to a damaging amount of radiation, requires guesswork and experimentation on the part of the practitioner, and, in the case of multicolored tattoos, may require multiple lasers. Through practice of the methods disclosed herein, tissue marking removal treatments can become essentially 100% effective and the associated costs of removal in terms of time (such as length of treatment course) and/or money can be reduced compared to standard tattoo removal treatment.

B. Removable Tattoo Inks

Aspects of the present disclosure relate to removable tissue marking compositions, such as micro-particles for use in removable tattoo inks Thus, disclosed is a removable tissue marking, such as a tattoo ink. The removable tissue marking composition includes colored micro-particles that comprise an internal core, comprising one or more bio-absorbable chromophores, and an outer shell. The disclosed micro-particles typically have a diameter of about 0.5-100 µm, but may be smaller or larger as long as the micro-particles can be implanted into a tissue to provide a tissue marking They can be spherical or any other shape. The outer shell of a disclosed micro-particle comprises at least one layer of polystyrene sulfonate (PSS) and at least one layer of polyallylamine hydrochloride (PAH). The outer shell is configured to maintain structural integrity during the implantation process, but rupturable by the application of electromagnetic radiation in the ultrasonic range. In some embodiments, the outer shell, comprises between about 2 and about 16 layers of polystyrene sulfonate (PSS) and polyallylamine hydrochloride (PAH) for example about 2, 3, 4, 5, 6, 7, 8, 9, 10, 11, 12, 13, 14, 15, or 16 layers of PSS and PAH. In some embodiments the PSS and PAH layers alternate. In some examples, the inner layer comprises PSS. In some examples, the outer layer comprises PSS. In some examples, the inner layer comprises PAH. In some examples, the outer layer comprises PAH. In some embodiments micro-particle further comprises a coating over the outer shell, such as polystyrene, for example high molecular weight polystyrene.

In some embodiments, the outer shell and/or coating is substantially visibly transparent such that the chromophore is detectable through the outer shell and/or coating.

In some embodiments, the micro-particles range in size from 0.1-100 µm, for example about 0.1 µm, 0.2 µm, 0.03 µm, 0.04 µm, 0.5 µm, 0.6 µm, 0.7 µm, 0.8 µm, 0.9 µm, 1.0 µm, 2.0 µm, 3.0 µm, 4.0 µm, 5.0 µm, 6.0 µm, 7.0 µm, 8.0 µm, 9.0 µm, 10.0 µm, 11.0 µm, 12.0 µm, 13.0 µm, 14.0 µm, 15.0 µm, 20.0 µm, 25.0 µm, 30 µm, 40 µm, 50 µm, 60 µm, 70 µm, 80 µm, 90 or 100 µm, such as between about 0.1 µm and about 5 µm, about 3 µm and about 15 µm, about 5 µm and about 20 µm, about 0.5 µm and about 50 µm, about 5 µm and about 70 µm and about 50 µm and about 100 µm in size. In specific embodiments, the micro-particle is from about 1 µm to about 10 µm in size.

In some embodiments, the micro-particle is suspended in a liquid carrier, for example alcohol, water, or glycerin, or any combination thereof, to facilitate implantation of the ink into the tissue of a subject.

The disclosed removable tattoo inks include one or more chromophores encapsulated within the outer shell. The chromophore can be of any colored material that has the properties of being bio-absorbable and non-toxic to the human, or animal body. Generally speaking, chromophores useful include stains, dyes, colored drugs and proteins, and other materials, such as those approved by the FDA for use within the body. Chromophores may be mixed in combinations before or during inner core formation, so that it may only be necessary to select a small number of different chromophores to obtain a broad range of colors for various tattoo purposes. For example, the pure chromophores can be mixed to form intermediate colors and shades. Thus, combinations of two or more chromophores can be mixed to form desired colors and shades, and then encapsulated to form micro-particles. Additionally or alternatively, different colored micro-particles can be mixed together to form a colored mixture. In one non-limiting example, blue micro-particles may be mixed with red micro-particles to form a purple tattoo ink mixture.

Useful bio-absorbable chromophores include: drugs and dyes such as rifampin (red), β-carotene (orange), tetracycline (yellow), indocyanine green (such as Cardio-Green®), Evan's blue, methylene blue; soluble inorganic salts such as copper sulfate (green or blue), $Cu(NH_3)^{2+}$ (dark blue), $MnO_4$ (purple), $NiCl_2$ (green), $CrO_4$ (yellow), $Cr_2O_7^{2-}$ (orange); proteins such as rhodopsin (purple and yellow forms) and green fluorescent protein (fluoresces green under blue light); and any of the Food and Drug Administration (FDA) approved dyes used commonly in foods, pharmaceutical preparations, medical devices, or cosmetics, such as the well-characterized non-toxic sodium salts FD&C Blue No. 1 (Brilliant Blue FCF), FD&C Green No. 3 (Fast Green FCF), FD&C Red No. 3 (Erythrosine), FD&C Red No. 40 (ALLURA® Red AC), FD&C Yellow No. 5 (Tartrazine), and FD&C Yellow No. 6 (Sunset Yellow FCF). Of these FD&C dyes, Yellow No. 5 is known to produce occasional allergic reactions. Additional FDA approved dyes and colored drugs are described in the Code of Federal Regulations (CFR) for Food and Drugs (see Title 21 of CFR chapter 1, parts 1-99). The table below lists a number of suitable chromophores, their Chemical Abstract Service (CAS) Registration Numbers, colors, and absorption maxima. Bio-absorbable chromophores for use in the disclosed compositions and methods are generally water-soluble at physiological pH, although fat-soluble chromophores (such as β-carotene) will also work if they are rapidly flushed from tissue, or digestible or metabolizable through enzymatic pathways (such as methylene blue, which is rapidly metabolized by mitochondrial reductases, and proteins which are digested by proteases). In some embodiments, the chromophore comprises a Food and Drug Administration (FDA)-approved dye. In some embodiments, the chromophore is selected from the group consisting of phthalocyanine dyes, cyanine dyes, and pyrylium dyes. In some embodiments, the chromophore comprises carbon black. In some embodiments, the chromophore is selected from the group consisting of rifampin, β-carotene, tetracycline, indocyanine green, Evan's blue, and methylene blue. In some embodiments, the chromophore is selected from the group consisting of FD&C Blue No. 2, FD&C Blue No. 1, FD&C Green No. 3, FD&C Red No. 3, FD&C Red No. 40, FD&C Yellow No. 5, and FD&C Yellow No. 6. In some embodiments, the chromophore comprises a soluble inorganic salt selected from the group consisting of copper sulfate, $Cu(NH_3)^{2+}$, $MnO_4$, $NiCl_2$, $CrO_4$, and $Cr^2O7^{2-}$.

The tattoo inks of the present disclosure can be used as tissue marking pigments for cosmetic, identification, and other purposes. For example the disclosed micro-particles can be are suspended in a liquid carrier, for example, alcohol, water, and/or glycerin, to form a tissue marking ink in the same manner as standard tattoo pigments.

The removable tattoo inks disclosed herein can be implanted into skin or similar superficial tissue with an electromagnetic coil tattooing machine (such as that disclosed in U.S. Pat. No. 4,159,659); a rotary permanent cosmetics application machine (such as that disclosed in U.S. Pat. No. 5,472,449); or with any manual tattooing device (such as the sterile single-use device marketed by Softap Inc., San Leandro, Calif.). Alternatively, the inks can be implanted using a non-invasive method, for example, as described in U.S. Pat. No. 5,445,611.

Tissue markings in skin must be properly placed to provide permanent markings Skin is composed of the outermost epidermis, generated by the constantly dividing stratum basale, and the underlying dermis. Dermal cells, such as fibroblasts, mast cells, and others, which do not generally replicate, are located within a resilient proteinaceous matrix. It is the upper dermis, below the stratum basale, into which the micro-particles are implanted to provide a tissue marking (such as a tattoo). After implantations, micro-particles in the dermis form part of a permanent tissue marking if they are phagocytosed by dermal cells or if they remain in the extracellular matrix.

In addition to skin, micro-particles of the invention can be implanted into a wide variety of living tissues comprising relatively stationary, infrequently-replicating cells. For example, the micro-particles can be implanted into the internal surfaces of the body that are contiguous with the external skin, including, but not limited to, the inner surfaces of the mouth and lips, the gums and tongue, inner surfaces of the eyelid, and the tissues lining internal body passages (such as the nasal, ear, anal, urethral, and vaginal passages, and the gastrointestinal tract). Other tissues that can be marked include the tissues of and/or under the fingernails and toenails, the dentin of the teeth, and the colored iris and white sclera of the eye.

As a result of their versatility, the micro-particles can be used to produce a wide variety of cosmetic tissue markings including decorative artistic tattoos that are removable and revisable; cosmetic makeup that is permanent as long as the wearer desires it; revisable corrective and reconstructive pigmentation as an adjunct to plastic surgery and to address other cosmetic problems, for example, to correct blotchy skin pigmentation or to mask thinning hair by adding pigment to the scalp; and reversible addition of pigment to small or large areas of the body purely for cosmetic reasons, for example, to create the look of a tan without exposure to ultraviolet rays.

In addition to marking skin, the micro-particles can be used to produce new cosmetic markings in other tissues. It is especially important that these new types of markings are removable to allow risk-free experimentation. For example, the micro-particles can be implanted into areas of externally visible non-skin tissue which are important to human appearance. Colored micro-particles can be added to the cornea or to the colored iris of the eye, for example, to change apparent eye color. White micro-particles which are highly light-scattering can be implanted into the dentin and/or sclera, for example, to whiten the teeth and/or eyes.

Colored micro-particles can be added to the tissue of and/or under the fingernails and/or toenails, for example, to create solid colors, patterns, or designs for decorative purposes. Identification markings made with the micro-particles can be changed, updated, and/or removed. In some cases, selectively detectable (such as normally invisible) micro-particles may be advantageous. Some examples of markings to fill identification needs include markings to assist tracking bodily sites of medical interest in external and superficial internal tissue, for example, marking a radiation therapy field on the skin, or marking a colon polyp in the intestine which can subsequently be monitored endoscopically; identification markings for humans, for example, emergency information regarding an individual's medical history, "dog-tags" on military personnel, and identification markings on newborn babies to ensure no hospital mix-ups; and identification markings for animals (such as wild animals, livestock, sport/show animals, and pets), for example, information markings for the return of lost pets.

C. Methods of Making Removable Tattoo Inks

Disclosed herein is a method of making a removable tattoo ink. The disclosed method includes forming an internal core, comprising one or more bio-absorbable chromophores and one or more salts with low water solubility. The internal core is coated to form an outer shell with at least one layer of polystyrene sulfonate (PSS) and at least one layer of polyallylamine hydrochloride (PAH), such as between 2 and 16 layers of PSS and PAH, such as 2, 3, 4, 5, 6, 7, 8, 9, 10, 11, 12, 13, 14, 15, or 16 layers of PSS and PAH. In some embodiments, the salt with low water solubility is removed form the inner core after encapsulation with the outer-shell, such that the inner core is substantially the one or more bio-absorbable chromophores.

In some embodiments, forming the internal core comprises mixing in solution the one or more bio-absorbable chromophores, $CaCl_2$ and $Na_2CO_3$, to form the internal core comprising $CaCO_3$ and the one or more bio-absorbable chromophores and removing the residual NaCl. For example, a solution of between about 0.1-10 M $CaCl_2$ (such as 0.1 M, 0.2 M, 0.3 M, 0.4 M, 0.5 M, 0.6 M, 0.7 M, 0.8 M, 0.9 M, 1.0 M, 1.5 M, 2.0 M, 2.5 M, 3.0 M, 3.5 M, 4.0 M, 4.5 M, 5.0 M, 6.0 M, 7.0 M, 8.0 M, 9.0 M or 10 M or anywhere in between) is mixed with a solution of between about 0.1-10 M $Na_2CO_3$ (such as about 0.1 M, 0.2 M, 0.3 M, 0.4 M, 0.5 M, 0.6 M, 0.7 M, 0.8 M, 0.9 M, 1.0 M, 1.5 M, 2.0 M, 2.5 M, 3.0 M, 3.5 M, 4.0 M, 4.5 M, 5.0 M, 6.0 M, 7.0 M, 8.0 M, 9.0 M or 10 M or anywhere in between) and one or more desired chromophores stirred for a period of time sufficient for the formation of micro-particles containing the desired chromophore(s) and $CaCO_3$, for example between 10 seconds and 10 minutes (such as about 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, or anywhere in between), although the solution can be stirred longer. In some embodiments, the formed micro-particles are washed to remove the non-incorporated chromophore(s) and NaCl, for example between about 1 and 10 times, although in certain applications, the micro-particles can be washed more than 10 times. In between each wash the micro-particles can be centrifuged to pellet the micro-particles and facilitate washes. In some examples the micro-particles are washed with acetone and then air dried.

In some embodiments, coating the internal core with at least one layer of polystyrene sulfonate comprises contacting the internal core comprising $CaCO_3$ and the one or more bio-absorbable chromophores with a solution comprising polystyrene sulfonate (PSS), for example contacting the $CaCO_3$ with a with a solution of about 0.1 to about 10 mg/mL PSS (such as about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.5 mg/mL, 2.0 mg/mL, 2.5 mg/mL, 3.0 mg/mL, 3.5 mg/mL, 4.0 mg/mL, 4.5 mg/mL, 5.0 mg/mL, 6.0 mg/mL, 7.0 mg/mL, 8.0 mg/mL, 9.0 mg/mL or 10 mg/mL or anywhere in between) from about 30 seconds to about 60 minutes (such as about 130 seconds, 40 seconds, 50 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 60 minutes, or anywhere in between), although longer times can be used. In some embodiments, coating the internal core with at least one layer of polystyrene sulfonate comprises contacting the internal core comprising $CaCO_3$ and the one or more bio-absorbable chromophores with a solution comprising polyallylamine hydrochloride (PAH), for example contacting the $CaCO_3$ with a with a solution of about 0.1 to about 10 mg/mL PAH (such as about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.5 mg/mL, 2.0 mg/mL, 2.5 mg/mL, 3.0 mg/mL, 3.5 mg/mL, 4.0 mg/mL, 4.5 mg/mL, 5.0 mg/mL, 6.0 mg/mL, 7.0 mg/mL, 8.0 mg/mL, 9.0 mg/mL or 10 mg/mL or anywhere in between) from about 30 seconds to about 60 minutes (such as about 130 seconds, 40 seconds, 50 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 60 minutes, or anywhere in between), although longer times can be used. This can be alternated, to create a micro-particle with multiple layers of PSS and PAH, such as between 2 and 16 layers of PSS and PAH, such as 2, 3, 4, 5, 6, 7, 8, 9, 10, 11, 12, 13, 14, 15, or 16 layers of PSS and PAH. In some embodiments, the $CaCO_3$ present in internal core is removed with a metal chelation agent, such as EDTA, EGTA and the like. Removal of the $CaCO_3$ creates a hollow micro-particle, where the hollow portion is filled with the chromophore.

D. Methods of Tattoo Removal

Because the micro-particle based tattoo inks of the current disclosure were designed to be rupturable using ultrasonic energy, the tattooed or marked tissue of a subject, that has been tattooed or marked with one or more of the tattoo inks comprising the micro-particles of the current disclosure, can be removed by the application of electromagnetic radiation in the ultrasonic range. By way of example, the ultrasonic energy is applied to the site of the tattoo to be removed and the ultrasonic energy ruptures the micro-particles present in the tattoo thereby releasing the contents of the micro-particles, which are absorbed by the body by virtue of being bio-absorbable.

The ultrasonic energy is applied using an external source for example using a commercially available ultrasound machine, such as available from Dynatronics, such as a Dynatron 360 at a specific or variable intensity and for a controlled length of time. The ultrasonic energy can be administered in one or several pulses. For example the ultrasonic energy can be administered in one or several sessions, such as sessions separated by minutes, days, weeks or even months, depending on such factors as the size of the tattoo for removal. In some embodiments, an area of a subject's tissue, such as an area of skin of the subject, is treated with ultrasonic energy between about 0.5 MHz and about 5 MHz at a power of between about 0.5 W/cm$^2$ to about 10 W/cm$^2$ for a period of about 1 minute to about 60 minutes. For example ultrasonic energy can be applied to the tissue of the subject that is between about 0.5 MHz and about 5.0 MHz, such as about 0.5 MHz, 0.6 MHz, 0.7 MHz, 0.8 MHz, 0.9 MHz, 1.0 MHz, 1.1 MHz, 1.2 MHz, 1.3 MHz, 1.4 MHz, 1.5 MHz, 2.0 MHz, 2.5 MHz, 3.0 MHz, 3.5 MHz, 4.0 MHz, 4.5 MHz, or 5.0 MHz, such as between about 0.5 MHz and about 2.0 MHz, between about 1.5 MHz and about 3.0 MHz, between about 0.5 MHz and about 4.0 MHz, or between about 2.5 MHz and about 5.0 MHz. The ultrasonic energy can be applied over a specific area, with a power dispersed over that area, for example with a power of between about 0.5 W/cm$^2$ to about 10 W/cm$^2$, such as about 0.5 W/cm$^2$, 0.6 W/cm$^2$, 0.7 W/cm$^2$, 0.8 W/cm$^2$, 0.9 W/cm$^2$, 1.0 W/cm$^2$, 1.1 W/cm$^2$, 1.2 W/cm$^2$, 1.3 W/cm$^2$, 1.4 W/cm$^2$, 1.5 W/cm$^2$, 2.0 W/cm$^2$, 2.5 W/cm$^2$, 3.0 W/cm$^2$, 3.5 W/cm$^2$, 4.0 W/cm$^2$, 4.5 W/cm$^2$, 5.0 W/cm$^2$, 6.5 W/cm$^2$, 6.0 W/cm$^2$, 6.5 W/cm$^2$, 7.0 W/cm$^2$, 7.5 W/cm$^2$, 8.0 W/cm$^2$, 8.5 W/cm$^2$, 9.0 W/cm$^2$, 9.5 W/cm$^2$, or 10.0 W/cm$^2$ such as between about 0.5 W/cm$^2$ and about 4.0 W/cm$^2$, between about 3.5, 8.5 W/cm$^2$, 9.0 W/cm$^2$ and about 6.0, W/cm$^2$, or between about 2.5 W/cm$^2$, and about 7.0 W/cm$^2$. Depending on the energy of ultrasonic energy being applied (e.g. the more power the less time), ultrasonic energy can be applied to the tattoo area from about 1 minute to about 60 minutes, such as about 1, 2, 3, 4, 5, 6, 7, 8, 9, 10, 15, 20, 25, 30, 35, 40, 45, 50, or 60 minutes. Such application can be continuous or as one of more pulses, for example to minimize heating and possible damage to the tissue of the subject. Such adjustments to the duration, power and frequency can be made by the user, such as practitioner or technician. Cells in the tissue may or may not be ruptured concomitantly, depending on the amount of energy applied and the pulse length in which it is delivered; after irradiation, chromophore dispersal occurs through physiological processes in both cases and the marking is removed from the tissue. The total systemic dose of the released chromophores (stains, dyes, drugs, or proteins) is generally low following a removal treatment.

In general, the total amount of radiation necessary to remove tissue markings of the invention can be reduced compared to standard laser therapy to remove standard tattoos because the electromagnetic absorption and/or structural properties of the micro-particles are carefully chosen in advance with removal in mind. This reduction means less secondary damage is incurred by surrounding cells, and patient pain is reduced.

Some patients may desire partial removal of a tissue marking which is also achieved by irradiation. Incomplete removal can be achieved, for example, by administering lower doses of radiation to affect only a fraction of micro-particles, or by only treating certain areas of the tissue marking. It may be desirable, for example, to reduce the size of the marking (such as to thin a cosmetic eyebrow or eyeliner); to remove a portion of a marking including a smaller mark, symbol, text, or identifying information (such as to remove a name from a vow tattoo); to reduce the color-intensity of a marking (such as to lighten a dark lipliner); or to transform the appearance of the tissue marking (such as to create a decorative light-on-dark pattern within a previously solid dark tissue marking).

In the event that a new tissue marking is desired to replace an existing marking, radiation is used to remove all or part of the original marking Colored micro-particles are then implanted into the tissue. The process could be used to update marks (such as bar codes), symbols, text, or identifying information, for example, to change a phone number marking on a pet after a move; to rework or refresh the appearance of the remaining tissue marking, for example, to add details to an artistic tattoo after regions have been removed to reduce the tattoo size; or to replace completely the original marking with a new tissue marking.

Example

This example demonstrates the manufacture, use and removal of the tattoo inks of the present disclosure.

The disclosed tattoo ink compositions (termed UltraInk™) were synthesized after several prototype iterations resulting in the current ink design which consisted of translucent micro-particle ink filled particles that are 10 microns in diameter equal in size and consistency to the current conventional permanent tattoo inks which are made of heavy metals. The relative size of the particle in the dermis makes the ink permanent because macrophage cells are unable to remove the particle from the dermis because it is too large for the macrophage to remove to the lymphatic system. The UltraInk™ inner core is synthesized with a combination of non-toxic bio-absorbable FD&C Blue No. 1 and a second color using FD&C Red No. 40. The bio-absorbable ink was used to create the colored micro-particle core with $Ca_2CO_3$ followed by clear encapsulation with polyallylamine hydrochloride (PAH) and polystyrene sulfonate (PSS). Once the micro-particle encapsulation was complete, the $Ca_2CO_3$ core was removed with EDTA leaving the liquid core of color inside the clear micro-particle or nanosphere. The ink was then ready for tattoo delivery using conventional tattoo needles and electric tattoo machines. Animals 1-4 received a 3 cm diameter red tattoo on one side of the flank and a second blue tattoo on the contralateral side performed by a professional tattoo artist with nearly 20 years experience. During Phase I, animals 1-4 were observed weekly under anesthesia in order to shave the skin and photograph the tattoos for objective changes including stability, intensity, infection, and loss of borders and patchiness. During Phase 2, animals 1-4 were treated weekly with varying intensity of external ultrasound (Dynatech) ranging from 0-3 MHz at an intensity of 2.0 for 10 minutes. Photography was also performed in order to document changes in intensity and resorption compared to the control animal which received 0 MHz.

The use of UltraInk™ by conventional delivery by a tattoo artist formed stable tattoos during the entire Phase I of the study and in Phase II in the control animal. There was no irritation, infection, or scabbing which is often reported following conventional tattoo ink application. An additional animal received tattoos with non-encapsulated coloring as a control for the effect of micro-particle encapsulation and had complete resorption of all color within 5 days. The remainder of the animals that received UltraInk™ tattoos had stable color and boarders during the initial 4 week period. Phase II of the study demonstrated immediate fading of the intensity of both the red and blue tattoos immediately after ultrasonic application as well as when observed and retreated one week later. The control animal which received 0 MHz sham ultrasound had no reabsorption of the tattoo. When encapsulated using nanosphere technology, the ink may remain permanently visible in the skin similar to conventional tattoo ink. Decay studies of the micro-particle half-life shows in preliminary studies that the tattoo may be permanent. If the individual desires removal of the tattoo, external ultrasonic energy has been shown in to remove the tattoo by mechanical lysis of the micro-particle into smaller particles thereby releasing the coloring that was spontaneously resorbed along with the smaller micro-particle fragments. Furthermore, from a cosmetic standpoint, the skin was normal in appearance, texture, and color after tattoo removal. Conventional laser tattoo removal often leaves the skin with abnormal pigmentation and often burned with partial removal of the tattoo leaving a smudged appearance often worse than the tattoo itself. If the individual desires to maintain the tattoo for a longer period, UltraInk™ can be used to re-tattoo the original design.

This study has described a detailed protocol to create and synthesize UltraInk using non-toxic coloring with a wide range of encapsulation layers. The synthesis of UltraInk™ was performed safely in a standard laboratory. This study demonstrates that use of UltraInk™ is the first documented report of a new substrate for tattoo ink that has created a long lasting tattoo using alternative ink synthesized by nanosphere technology. Furthermore, the animal study demonstrates that UltraInk™ can be removed using ultrasonic energy with clearly defined advantages over laser removal. UltraInk™ provides an option to conventional permanent tattoo inks providing future consumers with an alternative that may be permanent or removable which has tremendous advantages to meet the continued demand for tattoos in the younger population and the documented significant rate of regret and demand for tattoo removal in the maturing population.

Materials and Methods

The design for UltraInk™ is a based on a basic microcapsule structure that is between 1-10 μm in diameter using the biodegradable materials. The amounts that were used are found in Table 1. At this size, the microcapsule is easily applicable with a sterile needle but too large to diffuse through the dermal layer, ultimately shielding the dye from the body to prevent degradation.

TABLE 1

Reagents and equipment used for the synthesis of UltraInk ™

| Materials | Amount |
| --- | --- |
| $CaCl_2$ | 15 mL (0.5M) |
| $Na_2CO_3$ | 15 mL (0.5M) |
| PAH | 100 mg |
| PSS | 100 mg |
| EDTA | 15 mL (0.2M) |
| Polystyrene | 1.5 g |
| Food coloring | 100 mg |

Prototype of Microcapsules

In the first prototype, a clear microcapsule was created by first forming a $Ca_2CO_3$ core, surrounding the core with eight alternating layers of sodium polystyrene sulfonate (PSS) and poly(allylamine hydrochloride) (PAH) to form an outer shell, and then removing the core with EDTA to leave a hollow microcapsule, as shown in FIG. 1.

In the next two iterations of prototype development, a nontoxic bioresorbable food coloring, either FD&C Blue No. 1 or FD&C Red No. 40, was added during $Ca_2CO_3$ core formation. As with the first prototype, the core with either red or blue dye was subsequently surrounded by a range of 1 to 10 layers of PSS and PAH ending up with 8 alternating layers of PSS and PAH. For these prototypes, the $Ca_2CO_3$ core was not removed and left with the dye in the inner section of the microcapsule.

In the fourth prototype development, microcapsule synthesis was performed by having a solution of food coloring with no Ca₂CO₃ core surrounded by alternating layers of PSS and PAH to evaluate the spontaneous formation of a microcapsule and reduce the time and materials previously required. No microcapsules were formed with this method and the ink was shown to be well dispersed but not encapsulated throughout the water, which was an undesirable result.

To potentially reduce the diameter of the microcapsule, a fourth prototype was developed by performing micro-particle synthesis at 70° C. Both red and blue dyes were added to the Ca₂CO₃ core during core synthesis and the core was surrounded by eight alternating layers of PAH and PSS. However, final examination of these particles found that rod shapes formed instead of a spherical shape that was not as desired.

Figure 2:
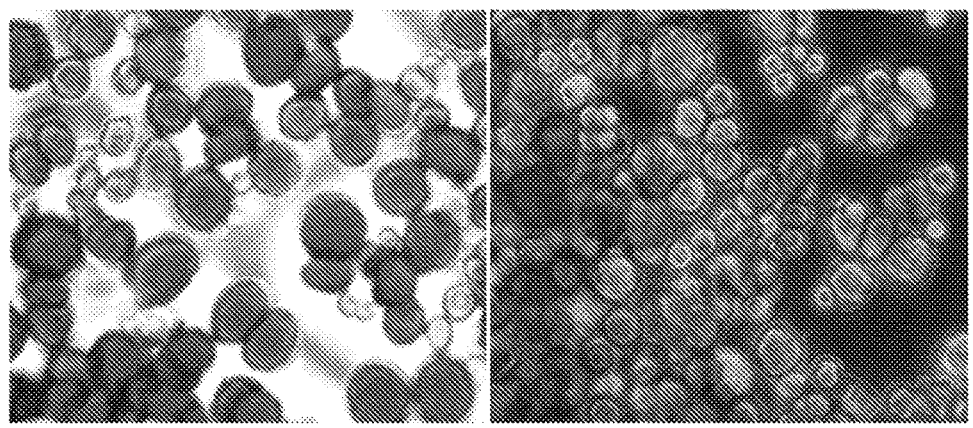
FIG. 2 is a pair of digital images showing red and blue colored micro-particles with the $Ca_2CO_3$ core removed.

The final and fifth prototype of micro-particle was developed following the same procedure as the second and third prototypes. Either red or blue dye was added during Ca₂CO₃ core synthesis, and the core was then surrounded by alternating layers of PAH and PSS. Unlike the earlier prototypes with dye, in the final prototype the Ca₂CO₃ core was removed with EDTA, leaving only the red or blue dye in the hollow core as seen below in FIG. 2. These microcapsules were determined to have superior color, appearance, and stability over previous prototypes. This was the composition and synthesis of UltraInk™ used during ultrasound testing.

Capsule Synthesis

Figure 3:
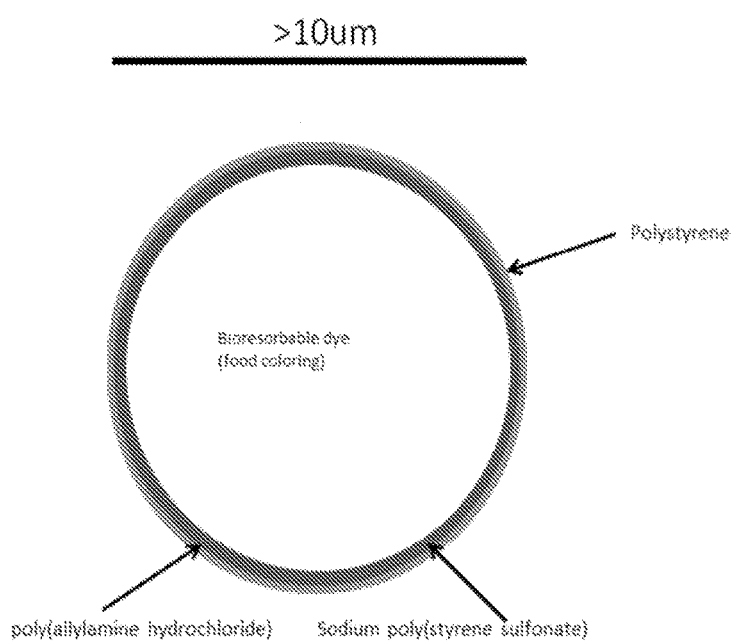
FIG. 3 is a schematic depiction of an exemplary embodiment of an UltraInk™ micro-particle with a chromophore in the hollow core, eight alternating layers of PAH and PSS, and an outer shell layer of high molecular weight polystyrene.

The final design solution for UltraInk™ utilizes several techniques developed with earlier prototypes. The final design is a microcapsule between 1-10 μm in diameter for reasons previously described. Microcapsule synthesis begins by mixing Na₂CO₃, FD&C food coloring or other bioresorbable dye, and CaCl₂ to form a solid Ca₂CO₃ core with color. Once this core is formed, eight alternating layers of PAH and PSS are added to form an outer shell, and EDTA is used to remove the Ca₂CO₃ so that just the food coloring remains in the core. Finally, once the core is removed, high molecular weight polystyrene is added to the micro-particle solution and is used to form an outermost shell around the alternating PAH/PSS layers. Overall, the final design will be similar to that shown in FIG. 3. High molecular weight polystyrene was included in the final design because it is a very stable polymer that will add stability to the UltraInk™ nanosphere micro-particle.

Testing and Results

Before any testing could be carried out, a standard curve was created using 1:10 serial dilutions of both the red and blue dyes and reading the absorbance levels with a plate reader. The two equations derived from a linear regression (r-squared>0.99) of the data points are shown below:

$$\text{Concentration of red dye}\left(\frac{g}{mL}\right) = \frac{AU - .0009}{6423.7}$$

$$\text{Concentration of blue dye}\left(\frac{g}{mL}\right) = \frac{AU - .00048}{4464.9}$$

These equations are both important in determining an unknown concentration of dye in a solution based on the absorbance.

Figure 4:
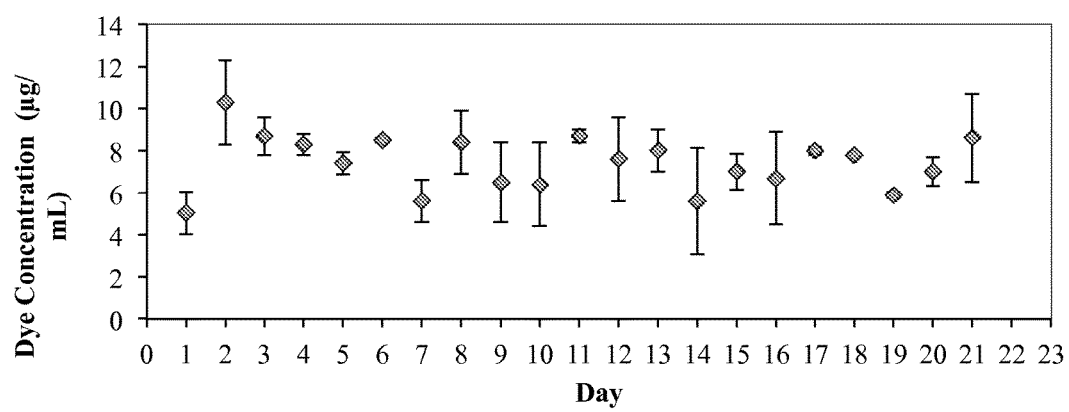
FIG. 4 is a bar graph showing dye concentration in supernatant as a function of time, demonstrating micro-particle stability.

Next, a leak study was conducted on the microcapsules. This test was designed to check the stability of the microcapsules. 7 mL of a 10 million capsules/mL solution was centrifuged at 1500 RPM. Since the particles would stick to the bottom, any leaked dye would remain the supernatant. This process was repeated over the course of 21 days as shown in FIG. 4. There was no upward trend in the concentration of dye in the supernatant, nor is there a significant increase in the amount of dye leaked from the microcapsules confirming physical stability at 21 days.

Ultrasound

Figure 5:
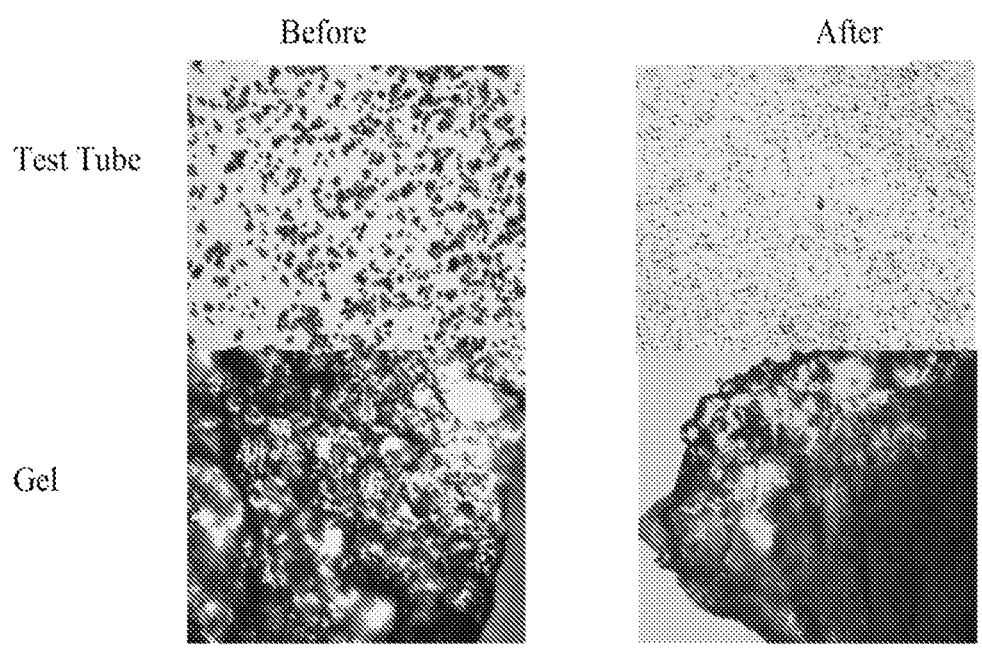
FIG. 5 is a set of digital images showing samples of dye-loaded micro-particles in a test tube and gel before and after ultrasonic treatment.

The first test for functionality of the particle involved observing if the particles were able to be weakened after treatment with ultrasonic energy. Micro-particles were placed into a test tubes and deposited into Perma-gel with a 6-pin tattoo needle. Samples were treated at 40 kHz in a 3 L, 50 W sonicator for 1, 5, 10, and minutes. At 10 minutes, the microcapsule nanospheres were no longer intact, see FIG. 5.

Figure 6:
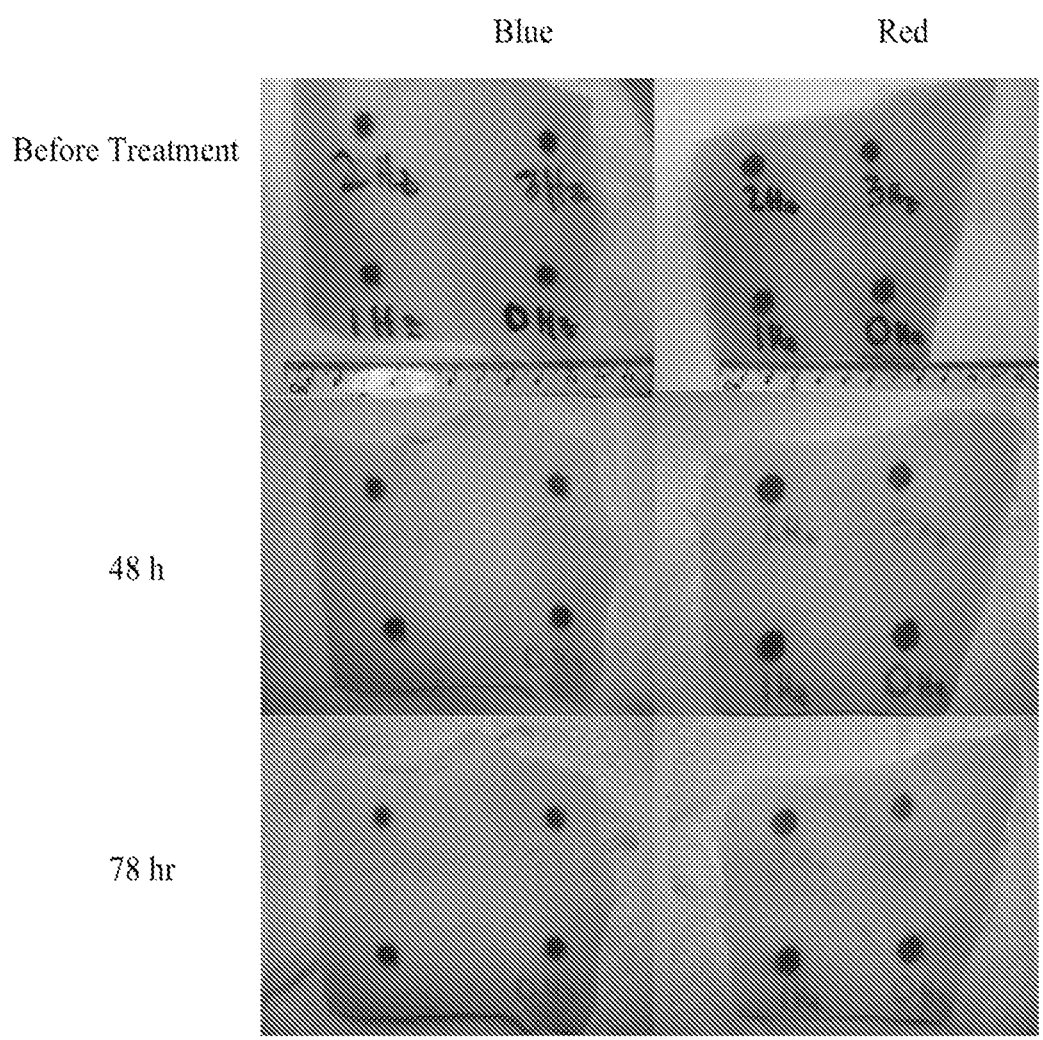
FIG. 6 is a set of digital images showing porcine skin samples of 0, 48, and 72 hrs after the use of ultrasound with the level of frequency labeled above. After 3 days, the blue and red tattoos visibly faded more when treated with higher frequencies of ultrasound. However, the spots treated at 1 MHz and 0 MHz were unaffected. After 3 days post treatment, the tattoos cease to fade any further in a non-living biologic model.

Next, a test was conducted to determine the effectiveness of external ultrasound (Dynatron 360) in removing a tattoo in a biologic model. Non-living cellular dermal and epidermal matrix of porcine skin was used since it is similar to human skin. 4 tattoos were treated with 0, 1, 2, and 3 MHz at a power of 3 W/cm² for 10 minutes. Pictures of the skin were taking prior to treatment, then in 3 hours intervals after treatment. The tattoos were noted for their brightness and intensity during this time, see FIG. 6.

Animal Testing

To further test the functionality of UltraInk™, 4 Sprague Dawley rats (6214, 6215, 6216, 6217) were tattooed and observed over a 12 week period. Sprague Dawley rats were used due to their light skin and short hair which facilitated shaving, application, and follow up evaluation of the tattoo. The main objectives of this phase of the study were to create a sustained tattoo in a live animal model using a conventional tattoo machine by an experienced tattoo artist and to then go on to observe the tattoo appearance over time as well as to begin the removal process with topical ultrasonic energy.

Tattoo Application

Figure 7:
FIG. 7 is a digital image showing a sample of tattoo immediately after it is deposited into rat 6216. The left side is the red tattoo and the right side is the blue tattoo.
Figure 8:
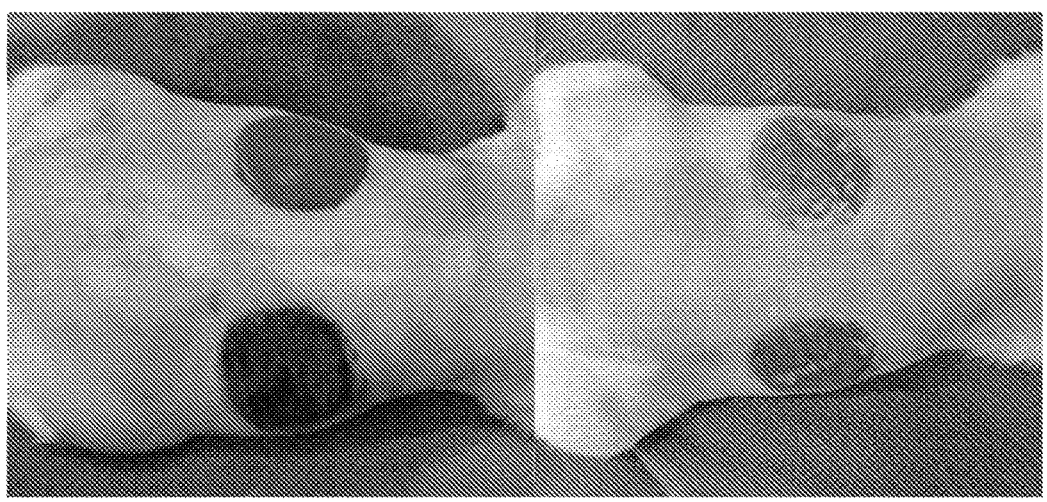
FIG. 8 is a set of digital images of sample tattoos on the skin of rats. The Left panel is a sample of tattoos immediately after it is deposited into rat 6216. The right panel is a sample tattoo after 8 weeks. The left side is the red tattoo and the right side is the blue tattoo.
Figure 9:
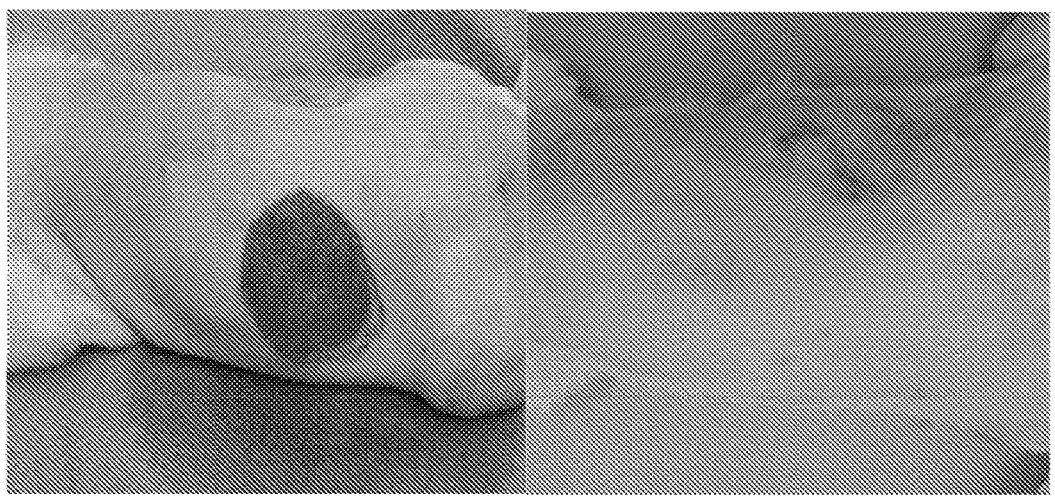
FIG. 9 is a set of digital images of sample tattoos on the skin of rats. The left panel is a sample of tattoos immediately after it is deposited into rat 6214. The right panel is a sample tattoo after 1 week in rat 6214. The left side is the red tattoo and the right side is the blue tattoo.
Figure 10:
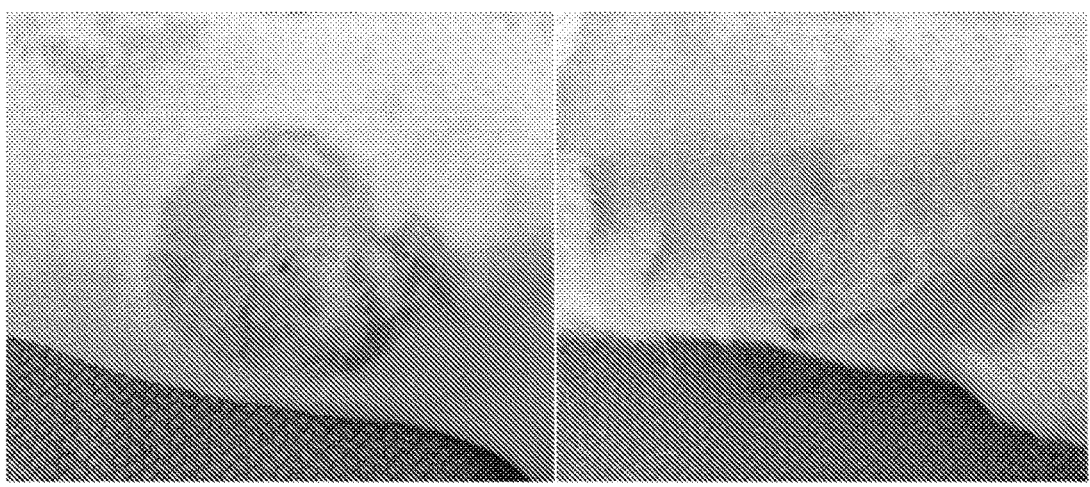
FIG. 10 is a set of digital images of sample tattoos on the skin of rats. The left panel is a sample of red tattoo after 2 weeks in rat 6217. The right panel is a sample of red tattoo after 7 weeks in rat 6217.

Each rat, under anesthesia, isoflurane (0-5%), was shaved and cleaned with green soap disinfectant prior to tattoo application. Rat 6214 was applied with one red 3 cm circle tattoo on the left side and one blue 3 cm circle on the right side. The ink contained three alternating layers of PAH and PSS. The ink had been synthesized in a cold centrifuge and stored in a refrigerator. The appearance of the ink and application of the ink appeared to be more consistent with the ink without encapsulation, which was thin and watery. Another layer of PSS was added for rat 6215. Rat 6215 received one red 3 cm circle tattoo of 4 alternating layers on the left side and no blue tattoo due to the time limitations (rats can only be under anesthesia for two hours). Rat 6216, the control, was administered one red 3 cm circle tattoo of 4 alternating layers on the left side and one blue 3 cm circle tattoo of 4 alternating layers on the right side FIG. 7. Rat 6217 was applied with one red 3 cm circle tattoo of 4 alternating layers on the left side and one blue 3 cm circle tattoo of 5 alternating layers on the right side, see FIG. 7.

The encapsulation process with nanosphere technology created an ink the consistency of conventional tattoo ink. This synthetic process also confirmed the creation of a tattoo in a live animal model with application of nanosphere technology. Each of four rats was tattooed by a professional tattoo artist with a red and blue circle 3 centimeters in diameter on its flanks A standard tattoo gun and needle were used per protocol with the rats under general anesthesia. The first four weeks of observation was to evaluate stability of the tattoo. Aquafor ointment was placed on the tattoos during the first week at daily intervals. There were no signs of infection, irritation, or animal self-mutilation.

Results

The integrity of the tattoos was observed and recorded qualitatively as photographs at weekly intervals. The UltraInk™ tattoo showed a very slight fade similar to standard tattoo ink, but overall maintained color, shape, and consistent intensity in the dermis at the end of the four week observation period. This represents the first reported confirmation of a tattoo using this nanosphere technology in the scientific literature.

The second phase of the study was removal of the tattoo with external ultrasound. On the fourth week, each rat was designated an ultrasound frequency of 0, 1, 2, or 3 MHz. The ultrasound was applied for a 10 minute interval to the red and the blue tattoos at an intensity of 2.0 w/cm$^2$ for all rats except the control which did not receive any ultrasound, 0 MHz. Photographs were taken of each rat before and after the treatments, and the tattoos immediately appeared to fade following treatment with 2 MHz demonstrating the most objective partial removal with no skin damage. The red tattoo was over 75% removed with the first 2 treatments with ultrasonic removal.

The blue tattoo which was treated with 3 MHz showed a 10-15% area of central necrosis from an apparent burn which may have been caused by the ultrasound overheating the central skin which received the most continuous ultrasonic energy demonstrating that this level, duration, or intensity may be too high.

Necrosis did not occur on the red tattoo at 3 MHz interestingly. The control rat tattoos which did not have ultrasound application did not demonstrate any fading. The rats underwent a second ultrasound treatment exactly one week following the first at the same frequency and intensity. This treatment showed further fading and removal of the UltraInk™ tattoos in all animals except the control. The tattoo in the control animal appears stable at 8 weeks.

Observations

Without ultrasound (Week 1-4)

After tattooing, the animals were observed for four weeks in one week intervals. Observations were made and photographs were taken on size, color density, dispersion of tattoo, and any possible infections or irritations.

With Ultrasound (Week 5-8)

After the initial four weeks of observations, animals were treated with ultrasound (Dynatron 150 plus) for tattoo removal. Each rat was treated with 10 minutes at a power of 2 W/cm$^2$ and each with a different frequency of either 0, 1, 2, 3 MHz, with no animal receiving the same frequency.

Observations

Without ultrasound (Week 1-4)

After tattooing, the animals were observed for four weeks in one week intervals. Observations were made and photographs were taken on size, color density, dispersion of tattoo, and any possible infections or irritations.

With Ultrasound (Week 5-8)

After the initial four weeks of observations, animals were treated with ultrasound (Dynatron 150 plus) for tattoo removal. Each rat was treated with 10 minutes at a power of 2 W/cm$^2$ and each with a different frequency of either 0, 1, 2, 3 MHz, with no animal receiving the same frequency.

Ultrasound continued (Week 9-12)

Micro CT Scan

UltraInk™ was studied in the test tube in vitro which demonstrated intact micro-particle. Use of the micro CT will also assist in evaluating the presence of micro-particle intact and disrupted in the dermis in vivo in the animals after sacrifice. Comparisons can be made between the ultrasound treated group and the control group to determine the efficacy of the ultrasonic treatment using another measurement. Furthermore, a decay curve can be used by evaluating the percentage of intact micro-particle immediately after tattoo and months after tattoo in order to determine the lifespan of the tattoo if no treatment is used.

DISCUSSION

The current study has demonstrated that a new tattoo ink UltraInk™ has been synthesized in a reproducible fashion and has been studied in every color. The use of nanosphere technology with layered encapsulation of dye and coloring can be used to administer a tattoo that may be permanent. Furthermore, the study has created a red and a blue tattoo in a rat model that is long lasting only when the dye is encapsulated. UltraInk™ was used successfully in this study to form a tattoo using new technology never before reported. In addition, the use of external ultrasound has demonstrated significant removal of the UltraInk™ tattoo which also may represent an important advance in the creation of a temporary tattoo.

Protocols

Absorbance Standard Curves

1. Make 150 µL with range of 0-1000 micro L of 1:10, 1:1000 . . . 1:1000000 dilutions of FD&C Blue No. 1 food coloring solution in distilled water.

TABLE 2

Timeline of ultrasound treatment on each Sprague Dawley Rat.

| Rat | Ultrasound-Power (W/cm$^2$) Week 5-8 Red and Blue Tattoo | Ultrasound-Frequency (MHz) | | | | | | | |
|---|---|---|---|---|---|---|---|---|---|
| | | Week 5 | | Week 6 | | Week 7 | | Week 8 | |
| | | Red Tattoo | Blue Tattoo | Red Tattoo | Blue Tattoo | Red Tattoo | Blue Tattoo | Red Tattoo | Blue Tattoo |
| 6214 | 2 | 1 | 1 | 1 | 1 | 1 | 1 | 1 | 1 |
| 6215 | 2 | 2 | 2 | 2 | 2 | 2 | 2 | 2 | 2 |
| 6216 | N/a | N/a | N/a | N/a | N/a | N/a | N/a | N/a | N/a |
| 6217 | 2 | 3 | 3 | 3 | N/a | 3 | N/a | 3 | N/a |

2. Transfer 100 μL with range of 0-1000 microL of each dilution into a clear 96-well plate. Add 100 μL with similar range above of distilled water to another well.
3. Read samples at 628 nm using the "shake setting" for one cycle and export data to Excel.
4. Read samples at a reference wavelength of 488 with the same settings in step 3.
5. To obtain the normalized AU, subtract the absorbance units obtained from reading the samples at the reference wavelength from the corresponding AU's obtained 628 nm. Then subtract the AU of distilled water from each value.
6. Formula: Normalized AU=(628 nm AU)-(488 nm AU)-(AU DIW 628 nm)
7. Plot the normalized data points against concentration of dye and perform a linear regression.
8. Repeat steps 1-6 but use FD&C Red No. 40 food coloring instead of blue and red samples at 504 nm instead of 628 nm.

Micro-Particle Synthesis

1. Mix 0.33 M $CaCl_2$ and 0.33 M $Na_2CO_3$ with ranges of 0-10 M each solutions and stir vigorously for 30 seconds. With ranges of 0-10 minutes.
2. Wash 4 times with range of 0-10 by centrifuging at 5000 RPM with range of 0-10000 RPM, removing supernatant, and then adding pure water.
3. Wash with acetone and then air dry.
4. Disperse Calcium Carbonate micro-particles in a solution of NaCl (0.5 m) with range of 0-10 m containing PSS (2 $mgmL^{-1}$) with range of 0-10 $mgmL^{-1}$ and shake for 10 minutes, with a range of 0-60 minutes
5. Wash twice with centrifugation and pure water with range of 1-10.
6. Add NaCl solution (0.5 m, 1 mL) with range of 0-10 m and 0-10 mL containing PAH (2 $mgmL^{-1}$) with range of 0-10 $mgmL^{-1}$ and continuously shaken for 10 min with range or 1-60 min, followed again by two centrifugation washing steps with range of 1-10.
7. Wash twice with centrifugation and pure water with range of 1-10 washes.
8. Repeat steps 1-4 3 more times with range of 1-10 times.
9. Shake coated $CaCO_3$ micro-particles for 30 min with range from 0-3 hours with EDTA solution (0.2 m, 1 mL, pH 5) with range of 0 to 10 m, 0-10 mL, and pH 3-7 followed by centrifugation and suspend in fresh EDTA solution (1 mL) with range of 0-10 ml.
10. To synthesize dye microcapsules, add 200 mg of FD&C Blue No. 1 or FD&C Red No. 40 powered food coloring in step 1.

Leak Study

1. Suspend micro-particles in 7 mL of distilled water. Final concentration should be $10 \times 10^6$ particles/mL. Ranges in concentration from $10 \times 10^1$ to $10 \times 10^{10}$
2. Centrifuge micro-particles at 1500 RPM for 5 minutes with range from 0-5000 rpm for 0-30 minutes.
3. Transfer 100 μL of supernatant from each batch to a clear 96-well plate. Add 100 μL of distilled water to 3 additional wells representing blank ranges from 0-1000 microL.
4. Read samples at 628 um using the "shake" setting and export data to Excel.
5. Repeat for 21 days.

Particle Sizing

1. Image microcapsules using a microscope.
2. Measure diameter of microcapsules using a micrometer or hemocytometer.

Ultrasound Testing in Perma-Gel and Pig Skin With Orthopedic Ultrasound

1. Mold Perma-gel block into discs 0.5 cm thick and 10 cm in diameter.
2. Using a 6-pin needle attached to a tattoo machine, deposit UltraInk™ in gel. Draw a solid circle with a 1 cm diameter.
3. Set ultrasonic device to 3 $W/cm^2$ at a frequency of 1, 2, or 3 MHz with ranges of 0-10 MHz studied and apply probe to surface of gel disks. Allow probe to remain on the surface for 10 minutes with time range from 0 to 1 hour.
4. After treatment, take images every 3 hours to observe change.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A removable tattoo ink, comprising colored micro-particles, wherein the micro-particles, comprise:
   an internal core, comprising one or more bio-absorbable chromophores,
   wherein the one or more bio-absorbable chromophores are water-soluble dyes, water-soluble pigments, or water-soluble drugs; and
   an outer shell, consisting of at least one layer of polystyrene sulfonate (PSS) and at least one layer of polyallylamine hydrochloride (PAH); and
   wherein the micro-particles further comprise a coating over the outer shell, wherein the coating comprises polystyrene;
   wherein the polystyrene coating and outer shell are rupturable by the application of ultrasonic energy.

2. The removable tattoo ink of claim 1, wherein the outer shell, consists of between 2 and 10 optionally alternating layers of polystyrene sulfonate (PSS) and polyallylamine hydrochloride (PAH).

3. The removable tattoo ink of claim 1, wherein the inner layer consists of polystyrene sulfonate or polyallylamine hydrochloride, and/or the outer layer consists of polyallylamine hydrochloride or polystyrene sulfonate.

4. The removable tattoo ink of claim 1, wherein the outer shell and/or coating is substantially visibly transparent such that the chromophore is detectable through the outer shell and/or coating.

5. The removable tattoo ink of claim 1, wherein the micro-particles range in size from 0.1 μm to 100 μm.

6. The removable tattoo ink of claim 1, wherein the micro-particle is suspended in a liquid carrier.

7. The removable tattoo ink of claim 6, wherein the carrier comprises alcohol, water, or glycerin, or any combination thereof.

8. The removable tattoo ink of claim 1, wherein the chromophore comprises a chromophore selected from:
   the group consisting of phthalocyanine dyes, cyanine dyes, and pyrylium dyes;
   the group consisting of water soluble forms of rifampin, β-carotene, tetracycline, indocyanine green, Evan's blue, and methylene blue;
   the group consisting of FD&C Blue No. 2, FD&C Blue No. 1, FD&C Green No. 3, FD&C Red No. 3, FD&C Red No. 40, FD&C Yellow No. 5, and FD&C Yellow No. 6, or a combination thereof;
   the group consisting of water soluble forms of copper sulfate, $Cu(NH_3)^{2+}$, $MnO_4$, $NiCl_2$, $CrO_4$, and $Cr_2O7^{2-}$, or a combination thereof.

9. A method of applying a tissue marking, the method comprising:
providing the removable tattoo ink of claim 1; and
implanting the ink into a tissue of a subject, thereby forming a tissue marking.

10. A method for rendering undetectable a tissue marking implanted in tissue, comprising subjecting a tissue marking formed from the removable tattoo ink of claim 1 to ultrasonic energy, for an intensity and duration sufficient to disrupt the micro-particles of the removable tattoo ink, thereby rendering undetectable the tissue marking implanted in tissue.

11. A method of making a removable tattoo ink, comprising:
forming an internal core, comprising one or more bio-absorbable chromophores, wherein the one or more bio-absorbable chromophores are water-soluble dyes, water-soluble pigments, or water-soluble drugs; and one or more salts with low water solubility; and
coating the internal core with at least one layer of polystyrene sulfonate (PSS) and at least one layer of polyallylamine hydrochloride (PAH), thereby forming an outer shell; and
coating the surface of the outer shell with polystyrene.

12. The method of claim 11, further comprising, removing the one or more salts with low water solubility, such that the inner core is substantially the one or more bio-absorbable chromophores.

13. The method of claim 11, wherein forming the internal core comprises mixing in solution the one or more bio-absorbable chromophores, $CaCl_2$ and $Na_2CO_3$, to form the internal core comprising $CaCO_3$ and the one or more bio-absorbable chromophores and removing the residual NaCl.

14. The method of claim 13, wherein coating the internal core with at least one layer of polystyrene sulfonate comprises contacting the internal core comprising $CaCO_3$ and the one or more bio-absorbable chromophores with a solution comprising polystyrene sulfonate (PSS).

15. The method of claim 13, wherein coating the internal core with at least one layer of polyallylamine hydrochloride comprises contacting the internal core comprising $CaCO_3$ and the one or more bio-absorbable chromophores with a solution comprising polyallylamine hydrochloride (PAH).

16. The method of claim 13, further comprising removing the $CaCO_3$ present in the internal core with a metal chelation agent.

17. The method of claim 16, wherein the metal chelation agent comprises EDTA.

* * * * *